United States Patent
Caivano et al.

(10) Patent No.: US 10,660,849 B2
(45) Date of Patent: May 26, 2020

(54) PHARMACEUTICAL FORMULATIONS COMPRISING OPIOID RECEPTOR AGONIST AS ACTIVE INGREDIENTS, METHODS OF MANUFACTURE AND THERAPEUTIC USES THEREOF

(71) Applicant: CHIESI FARMACEUTICI S.p.A., Parma (IT)

(72) Inventors: Grazia Caivano, Parma (IT); Ana Filipa Silva Borges, Tredegar (GB)

(73) Assignee: CHIESI FARMACEUTICI S.p.A., Parma (IT)

(*) Notice: Subject to any disclaimer, the term of this patent is extended or adjusted under 35 U.S.C. 154(b) by 0 days.

(21) Appl. No.: 16/164,282

(22) Filed: Oct. 18, 2018

(65) Prior Publication Data
US 2019/0117556 A1   Apr. 25, 2019

(30) Foreign Application Priority Data
Oct. 20, 2017   (EP) ..................................... 17197466

(51) Int. Cl.
| | |
|---|---|
| *A61K 9/00* | (2006.01) |
| *A61K 31/485* | (2006.01) |
| *A61K 47/38* | (2006.01) |
| *A61K 47/12* | (2006.01) |
| *A61K 9/08* | (2006.01) |
| *A61K 31/00* | (2006.01) |

(52) U.S. Cl.
CPC ................ *A61K 9/006* (2013.01); *A61K 9/08* (2013.01); *A61K 31/485* (2013.01); *A61K 47/12* (2013.01); *A61K 47/38* (2013.01); *A61K 31/00* (2013.01)

(58) Field of Classification Search
None
See application file for complete search history.

(56) References Cited

U.S. PATENT DOCUMENTS

| | | | |
|---|---|---|---|
| 5,601,077 A * | 2/1997 | Imbert | ................... A61M 11/00 128/200.14 |
| 6,677,346 B1 * | 1/2004 | Achari | ................. A61K 31/485 514/282 |
| 2001/0055569 A1 * | 12/2001 | Davis | ................... A61K 9/0043 424/43 |
| 2005/0085440 A1 * | 4/2005 | Birch | ................... A61K 9/0043 514/54 |
| 2007/0117828 A1 | 5/2007 | Simmons et al. | |
| 2015/0231191 A1 * | 8/2015 | Clarot | ................. A61K 36/515 424/758 |

(Continued)

FOREIGN PATENT DOCUMENTS

| | | |
|---|---|---|
| EP | 0 069 600 | 1/1983 |
| WO | 03/080022 A2 | 10/2003 |

OTHER PUBLICATIONS

Drugbank at https://www.drugbank.ca/drugs/DB00921 (retrieved from the interenet Jul. 10, 2019) (Year: 2019).*

(Continued)

*Primary Examiner* — Dennis Heyer
(74) *Attorney, Agent, or Firm* — Oblon, McClelland, Maier & Neustadt, L.L.P.

(57) ABSTRACT

Formulation comprising buprenorphine or a pharmaceutically acceptable salt thereof as the sole active ingredient, a viscosity enhancer, and a buffering agent in an amount to provide a pH of from 5.0 to 7.0 are useful for treating opioid withdrawal syndrome.

20 Claims, 2 Drawing Sheets

(56) References Cited

U.S. PATENT DOCUMENTS

2016/0175296 A1    6/2016    Baer, II et al.

OTHER PUBLICATIONS

Bhise et al. in Asian Journal of Pharmaceutics 201-215 (2008) (Year: 2008).*
Kraft et al. in Pediatrics 122:e601-e607 (2008) (Year: 2008).*
International Search Report in Application No. PCT/EP2018/078447 dated Jan. 24, 2019.
Written Opinion of the International Searching Authority in Application No. PCT/EP2018/078447 dated Jan. 24, 2019.
European Search Report in Application No. 17197466 dated Apr. 3, 2018.
W.K. Kraft et al., Pediatrics, vol. 122, No. 3 , ( 2008), pp. e601-e607.

* cited by examiner

PHARMACEUTICAL FORMULATIONS COMPRISING OPIOID RECEPTOR AGONIST AS ACTIVE INGREDIENTS, METHODS OF MANUFACTURE AND THERAPEUTIC USES THEREOF

CROSS REFERENCES TO RELATED APPLICATIONS

This application claims priority to European Patent Application No 17197466.0 filed on Oct. 20, 2017, which is incorporated herein by reference in its entirety.

BACKGROUND OF THE INVENTION

Field of the Invention

The present invention relates to pharmaceutical formulations comprising an opioid receptor agonist as active ingredient, methods of manufacture such a formulation, and therapeutic uses of such a formulation. The present invention more particularly relates to a buprenorphine formulation for buccal/sublingual administration providing a therapeutically effective dosage for the treatment of neonatal abstinence syndrome.

Discussion of the Background

Neonatal abstinence syndrome (NAS) is a complex of signs and symptoms in the postnatal period associated with the sudden withdrawal of maternally transferred opioids. The main manifestations include increased muscle tone, autonomic instability, irritability, poor sucking reflex, and impaired weight increase.

In epidemiologic studies, maternal opioid abuse is common, with toxicological evidence of use in about 1% of births (see Vega W A et al N Engl J Med 1993, 16:329(12), 850-854, which is incorporated herein by reference in its entirety). In addition, according to the Committee on Drugs of the American Academy of Pediatrics, NAS occurs in 55% to 94% of infants who are born to opioid-dependent mothers. The optimal treatment of NAS has not been established yet.

Specific opioid agents that are used include morphine sulfate, morphine in the form of neonatal opium solution, deodorized tincture of opium, and methadone.

Administration of morphine-based compositions has been reported to have lengths of treatment of 8 to 79 days, with a consensus duration of about 30 days. Said length of hospitalization is suboptimal because of interference with maternal bonding, potential for nosocomial infection, and resource use.

Therefore, there is a need for improved therapeutic agents that would safely decrease the length of hospitalization.

Buprenorphine is a partial µ-opioid receptor agonist that has found increasing use to treat opioid addiction in high dosages, to control moderate acute pain in non-opioid-tolerant individuals in lower dosages and to control moderate chronic pain in even smaller doses. The drug has a large first-pass metabolism in adults, and is then administered via the sublingual and buccal routes.

Buprenorphine has a number of characteristics that would make it an attractive agent in the treatment of NAS. For example, its long half-life and duration of action prevents the rapid change in receptor occupancy than can precipitate withdrawal symptoms. However, there has been little experience with the use of buprenorphine in neonatal or pediatric populations and limited information about the use of sublingual formulation in the newborns.

Furthermore, the therapeutically effective dosage in the newborns would be dependent on their weight and severity of maternal abuse. Therefore, fixed-dose film formulations for sublingual and buccal administration such as those commercially available or disclosed in EP 2 461 795, which is incorporated herein by reference in its entirety, could not be suitable as it will not be possible of promptly adjusting the needed amount of drug.

Kraft W et al reported the results of open label clinical trials in newborns for the treatment of opiate withdrawal (see Pediatrics 2008, 122(3), e601-607; Addiction 2010, 106, 574-580; N Engl. J Med 2017, 376:2341-2348, which are incorporated herein by reference in their entireties). The authors concluded that sublingual buprenorphine was safe with a substantial efficacy advantage over standard of care therapy with oral morphine. However, an extemporaneous solution formulation was used by mixing buprenorphine hydrochloride for injection in 30% ethanol and a simple syrup of sucrose. Final concentration was 0.075 mg/ml as buprenorphine free base. Due to the presence of ethanol, said formulation might not be suitable for repeated administration in human neonates.

Furthermore, if devoid of the proper viscosity, sublingual/buccal dosage forms in form of solution may deliver variable amounts of drug, as they will have poor retention at the site of application. In particular, given the volumes likely to be administered the recumbent position of the neonate after dosing, and use of a pacifier, the drug risks to be swallowed and absorbed through the gastrointestinal tract instead of through the sublingual route.

Other documents, i.e. EP 0 069 600, US 2007/117828, US 2016/175295, and WO 03/080022, all of which are incorporated herein by reference in their entireties, disclose buprenorphine-based formulations, but missing characteristics making them suitable for administration to neonates by sublingual route.

In view of the above considerations, there is still a need to develop a safer and effective formulation for sublingual administration to neonates having an adequate shelf-life for storage and use.

It would also be advantageous to provide a formulation with adequate viscosity to retain it under the tongue of the neonate or of the subject in need of treatment and in intimate contact with mucus membrane, avoiding swallowing and absorption through the gastrointestinal tract.

SUMMARY OF THE INVENTION

Accordingly, it is one object of the present invention to provide novel pharmaceutical formulations which contain an opioid receptor agonist as active ingredient.

It is another object of the present invention to provide novel pharmaceutical formulations which contain an opioid receptor agonist as active ingredient which are safe and effective formulation for sublingual administration to neonates having an adequate shelf-life for storage and use.

It is another object of the present invention to provide novel pharmaceutical formulations which contain an opioid receptor agonist as active ingredient with adequate viscosity to retain it under the tongue of the neonate or of the subject in need of treatment and in intimate contact with mucus membrane, avoiding swallowing and absorption through the gastrointestinal tract.

It is another object of the present invention to provide novel methods for the treatment of opioid withdrawal syndrome.

It is another object of the present invention to provide novel methods for the treatment of neonatal abstinence syndrome.

These and other objects, which will become apparent during the following detailed description, have been achieved by the inventors' discovery of the formulations and methods described below, Thus, in a first aspect, the present invention is directed to a ready-to-use pharmaceutical formulation in form of aqueous solution for sublingual and buccal administration, said formulation comprising:

(1) from 0.005 to 0.02% w/v of buprenorphine or a pharmaceutically acceptable salt thereof as the sole active ingredient;

(2) from 0.6% to 10% w/v of a thickening agent; and (3) a buffering agent in an amount to provide a pH of 5.0 to 7.0.

Its viscosity should be comprised between 500 and 2300 mPas, preferably between 700 and 2100 mPas at 25±2° C.

In a preferred embodiment of the invention, the thickening agent is a cellulose derivative, more preferably hydroxyethylcellulose (HEC) or sodium carboxymethylcellulose (NaCMC), even more preferably hydroxyethylcellulose.

In a second aspect, the present invention is directed to the afore-mentioned ready-to-use pharmaceutical formulation for use for the treatment of opioid withdrawal syndrome, preferably neonatal opioid withdrawal syndrome.

In a third aspect, the present invention is directed to the above ready-to-use pharmaceutical formulation in the manufacture of a medicament for the treatment of opioid withdrawal syndrome, preferably neonatal opioid withdrawal syndrome.

A fourth aspect of the present invention refers to a method of treating of opioid withdrawal syndrome in a patient in need thereof by administering the ready-to-use formulation of the invention for a period of 1 to 90 days, preferably of 3 to 70 days.

Preferably, the patient is a neonate affected by neonatal opioid withdrawal syndrome.

A fifth aspect of the present invention concerns a process for preparing the ready-to-use formulation of the invention.

A sixth aspect of the present invention concerns a syringe pre-filled with the ready-to-use formulation of the invention.

A seventh aspect of the present invention relates to a package comprising the pharmaceutical formulation of the invention in form of either ready-to-use aqueous solution or powder to be reconstituted in a suitable aqueous vehicle, in combination with a syringe, and instructions to orally administer said pharmaceutical formulation to a patient affected by opioid withdrawal syndrome.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

With reference to buprenorphine, the terms "drug," "active ingredient," and "active substance" are used interchangeably.

The terms "neonates," "newborns," and "infants" are used interchangeably.

The term "safe" means a pharmaceutical formulation suitable for sublingual administration, well tolerated by neonates, and devoid of excipients that could be harmful, antigenic or toxic for said patient population.

The term "buccal and sublingual administration" encompasses the mucosal regions, i.e. the pharmacological route of administration by which substances diffuse into the blood through tissues under the tongue through the oral mucosa (tissues which line the mouth), being the most commonly used for systemic drug delivery. The buccal/sublingual routes bypass the GI tract and hence drugs absorbed in this way bypass the liver and first pass metabolism and have direct access to the systemic circulation.

The term "pH microenvironment" refers to the pH of mouth region of the patient immediately surrounding the formulation.

For a ready-to-use formulation, the expression "physically stable" refers to a formulation that, under long-term conditions (25° C.±2° C., 60%±2% relative humidity), exhibits substantially no precipitation of the active ingredient and/or excipient during storage for at least one month.

Due to analytical difficulties related to the determination of an active ingredient at low concentration, the expression "chemically stable" refers to a formulation that, upon storage, shows a change in the buprenorphine content of not more than ±15% and no drug related degradation products in an amount higher than 5% upon storage for at least one month.

The term "bioequivalent" means obtaining 80% to 125% of the Cmax and AUC values for a given active ingredient in a different product.

The term "therapeutically effective amount" means the amount of the active ingredient, that, when delivered to neonates, provides the desired biological effect.

The term "treatment" refers to the therapeutic use for palliative, curing, symptom-allievating, symptom-reducing, disease regression-inducing therapy.

The term "essentially consisting of" is used to indicate a formulation comprising only a thickening agent and a buffering agent as essential excipients. For example it could comprise a sweetener and/or flavoring agent, but not excipients such as permeation enchancers.

Due to its activity on the opioid receptors, buprenorphine can successfully be used for the treatment of abstinence syndrome, particularly of neonatal abstinence syndrome.

Therefore, the aim of the present invention is to provide a safe pharmaceutical formulation for an efficacious treatment by sublingual administration to patients affected by opiate withdrawal syndrome (OWS), preferably neonates affected by neonatal OWS (hereinafter NOWS).

Said safe formulation shall comprise buprenorphine dissolved in an aqueous vehicle.

The formulations of the present invention may be administered to neonates as well as to children or adolescents.

The formulation of the present invention can be in form of a dry powder to be dissolved extemporaneously before use or in form of ready-to-use formulation.

In case it is dispensed as dry powder to be re-dissolved, it may be prepared according to known methods and it may be provided as a kit comprising a) the powdery pharmaceutical formulation; b) a pharmaceutically acceptable aqueous vehicle; c) a syringe; d) container means for containing the pharmaceutical formulation, the aqueous vehicle, and the syringe.

A ready-to-use formulation is preferably used.

Buprenorphine shall be utilized as a base or in the form of a pharmaceutically acceptable salt formed with an inorganic or organic acid, such as hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

Preferably, buprenorphine is present as the hydrochloride salt.

Advantageously, the concentration of the active ingredient shall be from 0.005 to 0.02% w/v, preferably 0.006 to 0.01% w/v, expressed as free base, based on the volume of the formulation.

In a particular embodiment of the invention, the concentration of buprenorphine hydrochloride is 0.0075% w/v, expressed as free base, based on the volume of the formulation.

The concentration of the thickening agent shall be comprised between 0.6% and 10%, w/v, preferably between 0.8% and 8.0% w/v, based on the volume of the formulation. The type and amount of the thickening agent shall be properly selected to achieve an adequate viscosity to retain the formulation as much as possible under the tongue of the patient, to minimize the absorption through the gastrointestinal tract. At the same time, the viscosity should be not too high to retard the release of the active ingredient from the matrix and hence, its local absorption.

More preferably, the concentration of the thickening agent could be between 1.0 and 6.0% w/v, based on the volume of the formulation.

In particular embodiments, said concentration is 1.0% w/v, or 1.5% w/v, or 2.0% w/v, or 6.0% w/v, based on the volume of the formulation.

Advantageously, the thickening agent may be selected from water-soluble polysaccharides such as alginates, carrageenans, pectin, water-soluble derivatives of cellulose: alkylcelluloses hydroxyalkylcelluloses and hydroxyalkylalkylcelluloses, such as methylcellulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP) and polycrotonic acids; also suitable are phthalated gelatin, gelatin succinate, crosslinked gelatin, shellac, water-soluble chemical derivatives of starch, cationically modified acrylates and methacrylates possessing, for example, a tertiary or quaternary amino group, such as the diethylaminoethyl group, which may be quaternized if desired.

Preferably, the thickening agent is a water soluble cellulose derivative selected from group consisting of hydroxyethylcellulose (HEC) or an alkali metal salt of carboxymethylcellulose (CMC) such as the sodium salt.

In fact, the thickening agents belonging to said classes could provide the suitable viscosity, while with other agents of the class of gums, such as xanthan gum, the viscosity of the formulation turned out to be too high.

Advantageously, the viscosity of the formulation at 25±2° C. shall be from 500 to 2300 mPas (1 mPas corresponds to 1 centipoise), preferably from 700 to 2100 mPas. The viscosity may be determined by any known method, for example using a rheometer.

Advantageously, the pH of the formulation of the present invention shall be from 5.0 to 7.0, more advantageously from 5.2 to 6.8, preferably from 5.5 to 6.5.

It has indeed been found that at pH higher than 7.0 the formulations of the invention may exhibit a lower chemical and physical stability.

Contrary to what reported in EP 2 461 795, which is incorporated herein by reference in its entirety, it has been found that said pH interval, avoiding the precipitation of the active ingredient into saliva, favors its absorption.

Without being limited by the theory, this may be due because no shift occurs with respect to the pH microenvironment (saliva/mucosa interface).

The results of a muco-adhesion test have also demonstrated that the formulations of the present invention are endowed with optimal property in terms of viscosity to allow its retention under the tongue of the patient without retarding the release of the active ingredient from the matrix, in particular when a water soluble cellulose derivative is used as thickening agent.

Furthermore, according to in-vitro permeation experiments, when a water soluble cellulose derivative is used, preferred formulations according to the invention shall have a pH of from 5.5 to 6.5 and an amount of thickening agent of from 1.0% to 2.0% w/v, even more preferably of 1.5% w/v, based on the volume of the formulation. The preferred thickening agent of this class shall be such as hydroxyethylcellulose. Said excipient is commercially available as Natrosol 250 HX™.

The in-vitro permeation tests simulate the passage of the drug across the oral mucosa and allow determination of its speed of release.

Any buffering agent able of providing the afore-mentioned pH maybe used, for example phosphate or citrate buffers as sodium or potassium salts. The skilled person in the art shall determine the proper amount.

In a preferred embodiment of the present invention, anhydrous citric acid and sodium citrate anhydrous is used as buffering agent.

The formulation of the present invention may also contain other excipients such as flavoring agents and/or sweeteners.

Flavoring agents may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

Other useful flavorings include aldehydes and esters such as benzaldehyde (cherry, almond), citral i.e., alpha-citral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The sweeteners may be chosen from the following non-limiting list: glucose (corn syrup), dextrose, invert sugar, fructose, and combinations thereof; saccharin and its various salts such as the sodium salt; dipeptide sweeteners such as aspartame; dihydrochalcone compounds, glycyrrhizin; *Stevia rebaudiana* (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof. Other sweeteners may also be used.

Typically, the skilled person in art shall select the sweetener and/or flavoring agent among those considered safe for neonatal administration.

Although not preferred, the formulations according to the invention may also contain permeation enhancers such as propylene glycol, and polyoxyl hydrogenated castor oil derivatives, for example polyoxyl 40 hydrogenated castor oil (commercially available as Kolliphor RH 40™).

In preferred embodiment of the present invention, the formulation has the following composition: 0.05 to 0.01% w/v buprenorphine hydrochloride expressed as a base, based on the volume of the formulation, 1.5% w/v hydroxyethylcellulose, based on the volume of the formulation, 0.12% w/v anhydrous citric acid, based on the volume of the formulation, 1.13% w/v sodium citrate anhydrous, based on the volume of the formulation, and water for injection. Its pH shall be of 6.0±0.3.

In an alternative preferred embodiment of the present invention, the formulation may have the following composition: 0.05 to 0.01% w/v buprenorphine hydrochloride expressed as a base, based on the volume of the formulation, 6.0% w/v sodium carboxymethylcellulose, based on the volume of the formulation, 0.12% w/v anhydrous citric acid, based on the volume of the formulation, 1.13% w/v sodium citrate anhydrous, based on the volume of the formulation, and water for injection. Its pH shall be of 6.0±0.3.

As it is described in more detail in the examples below, in an animal model of sublingual administration, the aqueous formulations having the aforementioned compositions turned out to be bioequivalent to the alcoholic formulation disclosed in Kraft et al., Pediatrics 2008, 122(3), e601-607, which is incorporated herein by reference in its entirety.

Without being limited by the theory, this appears rather surprising, as ethanol would normally favor the absorption.

Therefore, according to a preferred embodiment of the present invention, the formulation shall only consist of a pharmaceutically acceptable salt of buprenorphine as the sole active ingredient, a thickening agent, a buffering agent in a proper amount to provide a pH of 5 to 7.0, and optionally a flavoring agent and/or a sweetener.

The formulation according to the present invention can be prepared according to known methods.

In a particular embodiment, the formulations of the invention is prepared according to the following steps:
(i) dissolving a suitable amount of buprenorphine or a pharmaceutically acceptable salt thereof, preferably its hydrochloride salt, in water in a proper container to obtain a concentrated clear solution;
(ii) optionally, sterilizing the obtained solution in step (i) by filtration;
(iii) in parallel, dissolving the appropriate amount of a buffering agent in water in a suitable volumetric container until a clear solution is obtained;
(iv) optionally, sterilizing the obtained solution in step (iii) by heating;
(v) adding the appropriate volume of buprenorphine concentrated solution to the buffering agent solution to obtain the final desired concentration of buprenorphine, preferably 0.05-0.01 mg/mL (as free base) while mixing under continuous stirring; and
(vi) adding slowly the proper amount of the thickening agent to the solution of step (v) under continuous stirring until the thickening agent is completely dissolved and a clear, homogenous solution is obtained.

Preferably, water is water for injection (WFI).

In step (i) the concentration shall vary from 0.1 to 0.5 mg/ml, preferably from 0.2 to 0.4 mg/ml, more preferably of 0.324 mg/mL.

Advantageously, the container in steps (i) and (iii) could be made of any suitable material such as plastic or glass.

The sterilization procedures of step (ii) and (iv) shall be carried out according to methods known in the art.

In particular, the porosity of the filter in step (ii) and the temperature of heating in step (iv) shall be suitably adjusted by the skilled person.

The final formulation shall be distributed, under aseptic conditions, in the suitable containers.

Advantageously, the formulation according to the present invention may be used for the treatment of neonatal abstinence syndrome of any severity.

Preferably, the formulation of the invention may be used for the treatment of patients affected by opioid withdrawal syndrome (OWS) with or without exposure to other drugs, more preferably for the treatment of neonates affected by NOWS.

Typically, the buprenorphine dosage may vary between 10 and 80 micrograms/kg per day, preferably between 15 and 60 micrograms/kg per day, and it could be administered divided in two or more doses, preferably three doses for a period ranging from 1 to 90 days, preferably 3 to 70 days.

The dose and the duration of the treatment shall be anyway adjusted by the physician, depending on the weight of the neonate and the severity of the neonatal abstinence syndrome.

Typically, if used for the treatment of NOWS, the formulation is poured under the tongue by a syringe followed by insertion of a pacifier in the mouth of the neonate to reduce swallowing.

Any syringe available on the market of a volume comprised between 0.1 to 2.5 ml, more advantageously between 0.5 and 2.0 ml, could be used.

Syringes of 0.5 ml or 1.0 ml could preferably be used.

The syringe may be made of plastic, glass or any suitable material, preferably of plastic, more preferably of cyclo-olefin polymer (COP).

For example, syringes from Becton Dickinson (New Jersey, USA) could be suitable.

In a preferred embodiment of the invention, the ready-to-use formulation might be provided as pre-filled in a syringe, preferably in COP, and without a Luer lock.

For instance, suitable pre-fillable syringe are commercially available from Gerresheimer AG (Dusseldorf, Germany).

When they are used with neonates, said pre-fillable syringe shall be without a needle and endowed with a suitable cap, preferably big enough to avoid chocking of the neonate in case of its accidental ingestion.

In an alternative embodiment, a package comprising the pharmaceutical formulation of the invention in form of either ready-to-use aqueous solution or powder to be reconstituted in a suitable aqueous vehicle, in combination with a suitable syringe may be provided.

Other features of the invention will become apparent in the course of the following descriptions of exemplary embodiments which are given for illustration of the invention and are not intended to be limiting thereof.

EXAMPLES

Example 1

A first set of experiments was aimed at assessing the possibility of preparing buprenorphine aqueous solution formulations of adequate viscosity and pH in such a way as that they would turn out to be physically and chemical stable while maintaining a good profile of absorption.

The following formulations were prepared:

| Formulation 1 pH = 6.0 | Quantity per mL (mg) | Function |
| --- | --- | --- |
| Buprenorphine HCl | 0.075* | Active Principle Ingredient |
| Anhydrous Citric Acid | 1.22 | Buffering Agent |
| Sodium Citrate Anhydrous | 11.3 | Buffering Agent |
| Hydroxyethylcellulose | 15.0 | Thickening Agent |
| Water for Injection | 100 ml | Solvent |

| Formulation 2 pH = 6.0 | Quantity per mL (mg) | Function |
| --- | --- | --- |
| Buprenorphine HCl | 0.075* | Active Principle Ingredient |
| Anhydrous Citric Acid | 1.22 | Buffering Agent |
| Sodium Citrate Anhydrous | 11.3 | Buffering Agent |
| Sodium Carboxymethylcellulose | 60.0 | Thickening Agent |
| Water for Injection | 100 ml | Solvent |

| Formulation 3 pH = 7.2 | Quantity per mL (mg) | Function |
| --- | --- | --- |
| Buprenorphine HCl | 0.075* | Active Ingredient |
| Potassium phosphate bibasic | 2.28 | Buffering Agent |
| Potassium phosphate monobasic | 5.79 | Buffering Agent |
| Hydroxyethylcellulose | 15.0 | Thickening Agent |
| Water for Injection | 100 ml | Solvent |

| Formulation 4 pH = 7.2 | Quantity per mL (mg) | Function |
| --- | --- | --- |
| Buprenorphine HCl | 0.075* | Active Ingredient |
| Potassium phosphate bibasic | 2.28 | Buffering Agent |
| Potassium phosphate monobasic | 5.79 | Buffering Agent |
| Sodium Carboxymethylcellulose | 60.0 | Thickening Agent |
| Water for Injection | 100 ml | Solvent |

| Formulation 5 pH = 6.0 | Quantity per mL (mg) | Function |
| --- | --- | --- |
| Buprenorphine HCl | 0.075* | Active Ingredient |
| Anhydrous Citric Acid | 1.22 | Buffering Agent |
| Sodium Citrate Anhydrous | 11.3 | Buffering Agent |
| Hydroxyethylcellulose | 15.0 | Thickening Agent |
| Polyoxyl 40 Hydrogenated Castor Oil | 10.0 | Penetration enhancer |
| Water for Injection | 100 ml | Solvent |

| Formulation 6 pH = 6.0 | Quantity per mL (mg) | Function |
| --- | --- | --- |
| Buprenorphine HCl | 0.075* | Active Ingredient |
| Xanthan gum | 10.0 | Thickening agent |
| Potassium phosphate bibasic | 2.28 | Buffering Agent |
| Potassium phosphate monobasic | 5.79 | Buffering Agent |
| Water for Injection | 100 ml | Solvent |

*expressed as a base.

Analogous formulations to Formulation 1 were prepared using 0.5%, 1.0%, and 2.0% w/v hydroxyethylcellulose (Formulation 1', Formulation 1", Formulation 1''', respectively).

Corresponding formulations were prepared at buprenorphine HCl concentration of 0.01 mg/ml expressed as a base.

Furthermore, a Reference Formulation in ethanol according to the teaching of Kraft W et al Pediatrics 2008, 122(3), e601-607, which is incorporated herein by reference in its entirety, was prepared.

The Formulations 1, 2, 3, 4, and 5 exhibit a viscosity at 25±2° C. in the range of 700-2100 mPas (cP), while Formulation 6 exhibits a higher viscosity, i.e. 2500 mPas (cP). In aqueous solution, the latter formulation forms a sort of "soft gel" which persists as long as the system is not disturbed.

It was not possible to determine the viscosity of the reference formulation according to Kraft as the rheometer used to determine the viscosity of Formulations 1, 2, 3, 4, 5, and 6 is not appropriate for a liquid having a viscosity comparable to a Newtonian fluid.

Example 2

The Formulations 1, 2, 3, and 4 of Example 1 at a buprenorphine concentration of 0.01% w/v were stored for one month under long term conditions, i.e. 25±2° C. and 60% relative humidity, and under accelerated conditions, i.e. at 50±2° C., in order to evaluate their physical and chemical stability.

Stability was also tested under refrigerated conditions

The assay of buprenorphine and its impurities were performed by HPLC. The following parameters were also tested: pH, viscosity, and appearance. The results under long-term conditions are shown in Table 1. The results at 50°±2 C are shown in Table 2.

TABLE 1

Stability of Formulations 1, 2, 3, and 4 according to Example 1 under long-term conditions.

| | pH | Viscosity (mPas) | Total degradation products (%) | Assay % vs INITIAL | Appearance |
|---|---|---|---|---|---|
| Formulation 1 | | | | | |
| Initial (t = 0) | 6.0 | 2067 | 0.63 | 100 | Clear, colorless solution |
| t = 2 weeks | 6.1 | 1849 | 1.39 | 91.4 | Clear, colorless solution |
| t = 1 month | 6.0 | 1607 | 0.89 | 92.6 | Clear, colorless solution |
| Formulation 2 | | | | | |
| Initial (t = 0) | 5.8 | 1035 | 0.50 | 100 | Clear, colorless solution |
| t = 2 weeks | 5.8 | 1058 | 1.94 | 89.6 | Clear, colorless solution |
| t = 1 month | 5.8 | 1011 | 0.43 | 92.8 | Clear, colorless solution |
| Formulation 3 | | | | | |
| Initial (t = 0) | 7.1 | 1814 | 0.66 | 100 | Slightly hazy colorless solution |
| t = 2 weeks | 7.3 | 1798 | 1.58 | 92.3 | Slightly hazy colorless solution |
| t = 1 month | 7.2 | 1869 | 1.53 | 92.1 | Slightly hazy colorless solution |
| Formulation 4 | | | | | |
| Initial (t = 0) | 6.9 | 787 | 0.70 | 100 | Clear colorless to pale yellow solution |
| t = 2 weeks | 7.0 | 774 | 1.35 | 86.4 | Clear colorless to pale yellow solution |
| t = 1 month | 7.0 | 715 | 0.98 | 86.5 | Clear colorless to pale yellow solution |

TABLE 2

Stability of Formulations 1, 2, 3, and 4 according to Example 1 at 50 ± 2° C.

| | pH | Viscosity (mPas) | Total degradation products (%) | Assay % vs INITIAL | Appearance |
|---|---|---|---|---|---|
| Formulation 1 | | | | | |
| Initial (t = 0) | 6.0 | 2067 | 0.63 | 100 | Clear, colorless solution |
| t = 2 weeks | 6.0 | 1754 | 1.71 | 89.7 | Clear, colorless solution |
| t = 1 month | 5.9 | 1671 | 2.11 | 92.1 | Clear, colorless solution |
| Formulation 2 | | | | | |
| Initial (t = 0) | 5.8 | 1035 | 0.50 | 100 | Clear, colorless to pale yellow solution |
| t = 2 weeks | 5.9 | 814 | 3.08 | 87.9 | Clear, colorless to pale yellow solution |
| t = 1 month | 5.8 | 769 | 1.0 | 93.5 | Clear, colorless to pale yellow solution |
| Formulation 3 | | | | | |
| Initial (t = 0) | 7.1 | 1814 | 0.66 | 100 | Slightly hazy colorless solution |
| t = 2 weeks | 7.3 | 1785 | 1.51 | 91.3 | Slightly hazy colorless solution |
| t = 1 month | 7.2 | 1583 | 2.03 | 91.6 | Slightly hazy colorless solution |
| Formulation 4 | | | | | |
| Initial (t = 0) | 6.9 | 787 | 0.70 | 100 | Clear colorless to pale yellow solution |
| t = 2 weeks | 6.9 | 444 | 1.60 | 99.2 | Clear colorless to pale yellow solution |
| t = 1 month | 6.9 | 360 | 3.71 | 52.6 | Clear colorless to pale yellow solution with precipitate |

The results reported in Tables 1 and 2 show that no significant increase of total degradations products is observed in the formulations 1 and 2 at pH=6.0, and their amount remain well below the limit of 5.0%.

Notably, degradation products increases after 4 weeks at 50° C. in Formulation 4, while Formulation 3 appears to be hazy, indicating that a pH higher than 7 could not be optimal for chemical and physical stability.

Example 3

Formulations 1 and 2 at a buprenorphine concentration of 0.075 mg/ml expressed as a base, and the reference one were administered to dogs by sublingual administration.

Three male Beagle dogs were used and received all the treatments with one-week washout period. The formulations were administered by dispensing the dose (max. 2.5 mL) under the tongue to the sublingual region and then holding the mouth closed for ca 45 s. This procedure was repeated until the full dose volume (0.4 mL/kg) was administered.

Buprenorphine concentrations in dog plasma were determined by a validated HPLC-MS/MS bioanalytical method and used for comparing systemic exposure obtained by the three different formulations.

Figure 1:
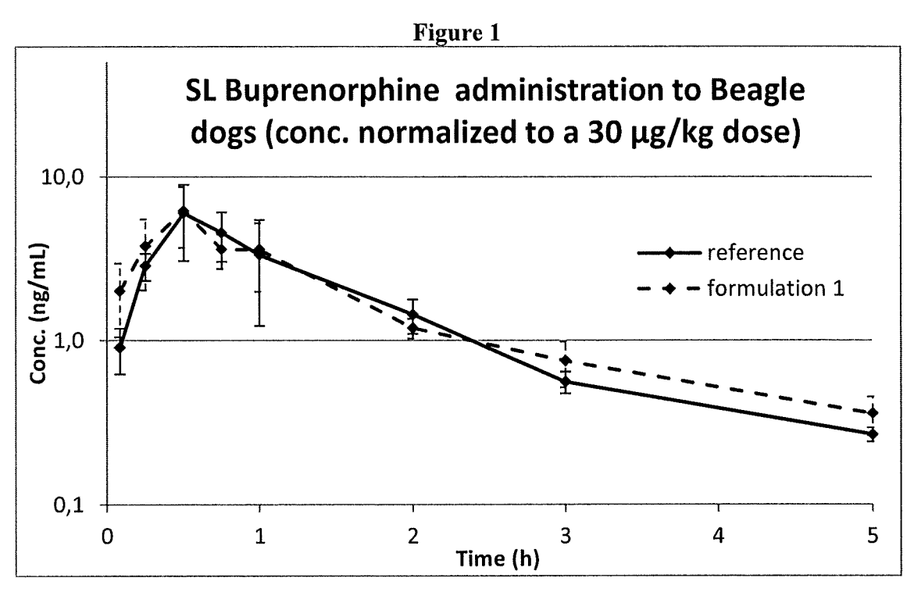
FIG. 1 shows a PK profile upon administration of formulation 1 of Example 1 versus reference formulation

As shown in FIG. 1, Formulation 1 and the Reference Formulation showed the maximum concentration at the same time and after dose normalization had almost equal maximum concentration and AUC.

Figure 2:
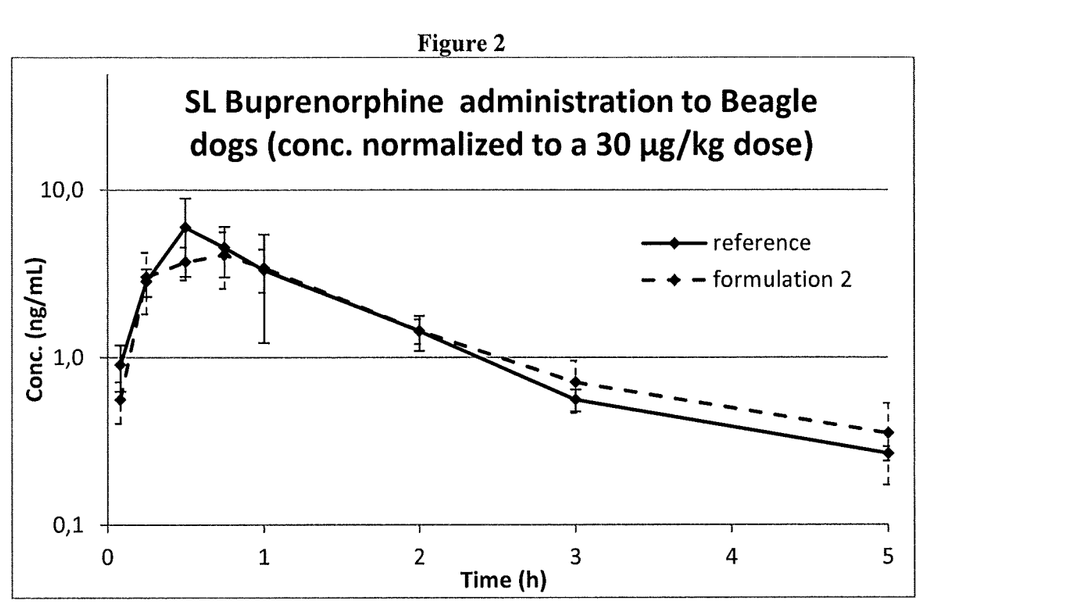
FIG. 2 shows a PK profile upon administration of formulation 2 of Example 1 versus reference formulation

Formulation 2 and the Reference Formulation are compared in FIG. 2: the time of the maximum concentration was on average observed slightly later for formulation 2 (0.75 vs 0.5 hours), and the maximum concentration and the AUC were slightly lower than in the reference formulation. The average relative bioavailabilities of Formulations 1 and 2 in comparison to the Reference Formulation were 110% and 102%, respectively.

Example 4

This study was designed to screen the in vitro performances of Formulations 1, 2, 3, 4, and 5 versus the Kraft Reference Formulation.

Experimental Procedure

Cuprophan (cellulose based membranes) contains glycerine as a humectant (to prevent drying and cracking). This was removed via prolonged soaking in distilled water.

The membranes (pre-trimmed 22 mm diameter circles were prepared) were placed in a 500 ml Duran bottle for soaking and the contents mixed via rotation (20 rpm). Two further complete changes of water were performed to eliminate the glycerine. Total soaking/rinsing time was ~46 hours prior to the release study.

The Cuprophan membranes were mounted as a barrier between the halves of individually numbered and lightly greased (high vacuum grease, Dow Corning, USA) horizontal Franz-type diffusion cells, with the stratum corneum facing the donor chamber. The area available for diffusion was about 1.2 cm$^2$, with the exact area and volume (averaging ~3.4 ml) having been previously measured for each individual diffusion cell.

The receptor chambers of the diffusion cells were filled with a known volume of temperature equilibrated 1% (w/v) Brij O20 in pH 7.4 phosphate buffered saline (BPBS) and capped. The diffusion cells were immersed in a constant temperature water bath such that the receptor chambers were maintained at 37.0±0.5° C. throughout the experiment. Receptor chamber contents were continuously agitated by small PTFE-coated magnetic followers driven by submersible magnetic stirrers. Cells were allowed to equilibrate prior to dosing (≥75 minutes).

The test formulations were applied to the membrane surface at a dose of 500 μl/cm$^2$ using a Microman M1000 positive displacement pipette. Care was taken to ensure complete surface coverage was obtained no air bubbles). Donor chambers were occluded using Parafilm (Nesco) immediately after dosing. Three replicates were run for each active formulation and there were six control cell, each dosed with a separate placebo formulation. The exact time of application was noted and that time represented zero time for that cell. Dosing times were very closely monitored due to the rapid sampling time points.

The applied formulation doses were equated to 37.5 μg/cm$^2$ buprenorphine HCl for all active cells.

100 μl samples were taken (using a digital pipette) from each receptor chamber 15 and 30 minutes after dosing. The liquid removed was only replaced following the 30 minutes sample. 200 μl receptor phase samples were then taken 60 and 120 minutes after dosing. Each sample was placed into a pre-labelled 200 μl tapered glass vial (Agilent, Cheadle, UK) and a cap (PTFE lined septum) immediately applied prior to freezing the vial (–20° C.) pending analysis.

Following removal of the 200 μl receptor phase samples taken after 120 minutes, the remaining receptor phases were removed and placed in 20 ml glass vials (Chromacol, UK) that were then capped and frozen (–20° C.) for assay validation purposes.

An ultra-high performance liquid chromatography (UHPLC) assay with UV detection was used to analyze samples for buprenorphine content.

Receptor phase samples (in 200 μl vials and stored at –20° C.) were prepared for analysis as follows. Vials were allowed to defrost at room temperature prior to thorough vortexing. The vials were then centrifuged (3 minutes at 10,000 rpm) and transferred to the autosampler.

The recovery of buprenorphine from 2 hr receptor phase samples was assessed through spiking studies using the bulk receptor phase (stored in 20 ml vials), samples (one cell from each active and control group) were spiked by the addition of a small aliquot of calibration solution (spike concentration 2.00 μg/ml). Following the analysis of spiked and unspiked samples, the recovery of buprenorphine was calculated following subtraction of the contribution from the receptor phase. Average spike recovery was 100.2% (0.79% RSD, n=17) and a similar value was obtained from spiking BPBS alone. The results are reported in Table 3.

TABLE 3

Buprenorphine HCl permeation data (μg/cm$^2$, mean ± SE, n = 3)

| Formulation | 15 min | | 30 min | | 60 min | | 120 min | |
|---|---|---|---|---|---|---|---|---|
| | Mean | SE | Mean | SE | Mean | SE | Mean | SE |
| Kraft Reference | 0.895 | 0.034 | 3.04 | 0.11 | 5.47 | 0.19 | 9.27 | 0.10 |
| Formulation1 | 2.16 | 0.12 | 4.13 | 0.02 | 6.51 | 0.23 | 10.3 | 0.1 |
| Formulation 2 | 0.414 | 0.036 | 0.988 | 0.061 | 1.90 | 0.10 | 3.52 | 0.15 |
| Formulation 3 | 1.37 | 0.06 | 2.85 | 0.09 | 5.53 | 0.34 | 11.0 | 0.3 |
| Formulation 4 | 0.000 | 0.000 | 0.448 | 0.025 | 0.829 | 0.047 | 1.70 | 0.12 |
| Formulation 5 | 0.430 | 0.020 | 0.822 | 0.008 | 1.44 | 0.02 | 2.39 | 0.04 |

As it can be appreciated, release rates were better from Formulations 1 and 3 than from the Formulations 2 and 4 having a pH higher than 7.0.

The release from Formulation 1 comprising HEC was more rapid than both the Formulation 3 comprising NaCMC and the Kraft Reference Formulation.

The inclusion of the penetration enhancer greatly reduced the release.

Example 5

Mucoadhesion Properties Evaluation

Mucoadhesion properties of the formulations of the invention were tested by means of the "inclined plane" apparatus as reported in Pescina, S., et al., Drug Dev Ind Pharm, 2017. 43(9): p. 1472-1479, which is incorporated herein by reference in its entirety.

The Formulations 1, 1', 1" and 1'" of Example 1 were used for the experiment.

Approx. 30 mg, accurately weighted, of each formulation were applied on the esophageal epithelium (1.13 cm$^2$) previously glued on the Petri dish (9 cm$^2$) inclined at 45° C. The simulated salivary fluid (SSF, NaCl 8 g/L, Na$_2$HPO$_4$ 2.38 g/L, KH$_2$PO$_4$ 0.19 g/L, pH 6.8) was flushed onto the formulation at 1 ml/min flow rate, using a syringe pump. The solution was collected at predetermined time points and injected in HPLC for the evaluation of the drug washed away.

The results are reported in Table 4 wherein the effect of viscosity (expressed as % of thickening agent) on the % of buprenorphine washed away from the mucosa is reported.

The viscosity of the formulation seems to be critical only at 0.5% (when after 1 min 60% of the formulation is washed away from the mucosa, while the formulations comprising 1%, 1.5% and 2.0% of thickening show good mucoadhesion properties.

TABLE 4

| Time (min) | 0.5% | 1% | 1.5% | 2% |
| --- | --- | --- | --- | --- |
| 1 | 62.0 | 40.1 | 35.4 | 40.5 |
| 2 | 15.2 | 23.5 | 17.5 | 24.8 |
| 3 | 4.5 | 14.9 | 8.6 | 7.6 |
| 4 | 2.7 | 11.9 | 5.3 | 7.7 |
| 5 | 1.6 | 11.9 | 5.2 | |
| 6 | 0.7 | 9.4 | 4.0 | |
| 7 | 0.4 | 8.7 | 2.4 | |
| 8 | 0.2 | 5.7 | 1.9 | |

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A pharmaceutical formulation in the form of an aqueous solution for sublingual or buccal administration, said formulation comprising:
   (1) from 0.005 to 0.02% w/v, based on the volume of the formulation, of buprenorphine or a pharmaceutically acceptable salt thereof as the sole active ingredient;
   (2) from 0.6 to 10% w/v, based on the volume of the formulation, of a thickening agent; and
   (3) a buffering agent in an amount sufficient to provide a pH of 5.0 to 7.0,
   wherein said formulation has a viscosity of from 500 to 2300 mPas at 25±2° C.

2. The formulation according to claim 1, wherein said buprenorphine is in form of its hydrochloride salt.

3. The formulation according to claim 1, which has a pH of from 5.2 to 6.8.

4. The formulation according to claim 1, which has a pH of from 5.5 to 6.5.

5. The formulation according to claim 1, which has a viscosity of from 700 to 2100 mPas at 25±2° C.

6. The formulation according to claim 1, wherein said thickening agent is a cellulose derivative.

7. The formulation according to claim 6, wherein said thickening agent is hydroxyethylcellulose or sodium carboxymethylcellulose.

8. The formulation according to claim 1, wherein said buffering agent is made of citric acid and sodium citrate.

9. The formulation according to claim 1, which further comprises a sweetener and/or a flavoring agent.

10. A pharmaceutical formulation in the form of an aqueous solution, consisting essentially of:
   0.05-0.01% w/v, based on the volume of the formulation, of buprenorphine hydrochloride expressed as a base;
   1.5% w/v, based on the volume of the formulation, of hydroxyethylcellulose or 6.0% w/v, based on the volume of the formulation, of sodium carboxymethylcellulose;
   0.12% w/v, based on the volume of the formulation, of anhydrous citric acid;
   1.13% w/v, based on the volume of the formulation, of sodium citrate anhydrous; and
   water for injection.

11. A process for preparing a formulation according to claim 1, comprising:
   (i) dissolving a suitable amount of buprenorphine or a pharmaceutically acceptable salt thereof in water in a glass container to obtain a buprenorphine concentrated clear solution;
   (ii) optionally, sterilizing the obtained solution in step (i) by filtration;
   (iii) in parallel, dissolving an appropriate amount of a buffering agent in water in a volumetric glass container to obtain a clear buffering agent solution;
   (iv) optionally, sterilizing the obtained solution in step (iii) by heating;
   (v) adding an appropriate volume of buprenorphine concentrated solution to said buffering agent solution to obtain a final desired concentration of buprenorphine while mixing under continuous stirring; and
   (vi) slowly adding a proper amount of a thickening agent to the solution of step (v) under continuous stirring until the thickening agent is completely dissolved and a clear and homogenous solution is obtained.

12. A method of treating opioid withdrawal syndrome, comprising administering to a subject in need thereof an effective amount of a formulation according to claim 1.

13. The method according to claim 12, wherein said opioid withdrawal syndrome is neonatal opioid withdrawal syndrome.

14. A syringe pre-filled with a formulation according to claim 1.

15. A package, containing a formulation according to claim 1 in combination with a syringe, and instructions to orally administer said pharmaceutical formulation to a patient suffering from opioid withdrawal syndrome.

16. The package according to claim 15, wherein said patient is a neonate suffering from neonatal opioid withdrawal syndrome.

17. A method of treating opioid withdrawal syndrome, comprising administering to a subject in need thereof an effective amount of a formulation according to claim 10.

18. The method according to claim 17, wherein said opioid withdrawal syndrome is neonatal opioid withdrawal syndrome.

19. A syringe pre-filled with a formulation according to claim 10.

20. A package, containing a formulation according to claim 10 in combination with a syringe, and instructions to orally administer said pharmaceutical formulation to a patient suffering from opioid withdrawal syndrome.

* * * * *